United States Patent [19]

Merick et al.

[11] Patent Number: 5,205,322
[45] Date of Patent: Apr. 27, 1993

[54] METHOD AND APPARATUS FOR FLOW CONTROL FOR SENSOR CALIBRATION

[75] Inventors: Ed Merick, Stow, Mass.; Al Signorelli, Encinitas, Calif.

[73] Assignee: Puritan-Bennett Corporation, Carlsbad, Calif.

[21] Appl. No.: 900,010

[22] Filed: Jun. 17, 1992

[51] Int. Cl.⁵ .............................................. F16K 11/24
[52] U.S. Cl. ...................................... 137/597; 73/1 G; 137/607; 137/613
[58] Field of Search ............... 137/606, 607, 595, 613, 137/113, 597; 73/1 G

[56] References Cited

U.S. PATENT DOCUMENTS

| | | | |
|---|---|---|---|
| 3,247,702 | 4/1966 | Houser et al. | 73/1 G |
| 3,809,109 | 5/1974 | Breiling et al. | 137/607 X |
| 4,209,300 | 6/1980 | Thibault | 73/1 G |
| 4,247,018 | 1/1981 | Credle | 137/113 X |
| 4,630,038 | 12/1986 | Jordan | 73/1 G X |

Primary Examiner—Stephen M. Hepperle
Attorney, Agent, or Firm—Fulwider, Patton, Lee & Utecht

[57] ABSTRACT

The improved gas flow control apparatus controls the flow of multiple gases to a tonometer for calibration of a blood gas or pH sensor and compensates for the failure of gas supply solenoid valves to operate properly in controlling gas flow. Intermediate gas supply solenoid valves select between gas flow of the supplied gas in an open position, and venting to the atmosphere in a closed position. A common selector valve is also provided in the gas flow path to the tonometer to select gas flow from one of the intermediate gas flow valves. A control unit is provided for controlling the operation of the intermediate and common selector valves.

13 Claims, 3 Drawing Sheets

METHOD AND APPARATUS FOR FLOW CONTROL FOR SENSOR CALIBRATION

BACKGROUND OF THE INVENTION

1. Field of the Invention

This invention relates generally to gas and pH measurement technology, and more particularly concerns an automated system for controlling the flow of gases for tonometric calibration of biomedical blood gas and pH sensors.

2. Description of Related Art

Accurate measurement of pH and the partial pressures of carbon dioxide and oxygen in the blood have become important in modern medicine, particularly for monitoring the respiratory condition of a patient. Extremely small multiparameter optical sensors have been developed for taking intravascular measurements of acidity, carbon dioxide and oxygen levels in the blood. Such sensors allow remote measurement of these parameters when combined with compatible intravascular catheter systems. Onsite calibration of such sensors before use in a medical setting is important, and it is desirable to provide automated systems for doing so.

Conventional systems for automatic tonometric calibration of gas sensors typically control the flow of calibration gases to the tonometer with electrical solenoid valves. In a typical gas flow control system for automated tonometry, the required gases are supplied from cylinders of calibration gases compressed under high pressure, through flow regulators and gas supply lines to a normally closed solenoid valve. For calibration of sensors which can sense multiple gas and/or pH conditions, the separate flow of two or more gas mixtures can be controlled by opening the valves as desired to allow flow through a manifold to the tonometer, to produce known gas concentrations and pH conditions in the tonometer.

The solenoid valves employed in such automatic tonometric systems generally include an electromagnet coupled to a metal plunger which has a resilient valve seat. The plunger is normally biased to a closed position by a spring, so that energization of the electromagnet acts to pull the plunger away from the valve seat, opening the valve to allow gas flow. Under ideal conditions such solenoid valves generally operate well in controlling gas flow over desired ranges of pressure and flow rates. However, incorrect seating of such valves, caused by such factors as degradation of the spring force over extended periods of time, or the lodging of metal or dust particles between the valve seat and the plunger, can allow gas leakage when the valve is supposed to be closed. In a situation where two or more gas compositions are separately introduced into a tonometer, failure of a valve to properly close can allow entry into the tonometer of a mixture of a first calibrating gas which is supposed to be turned off and a second calibrating gas which is turned on. Such an introduction of mixed calibration gases into the tonometer can cause significant errors in tonometric calibration which are not readily detectable.

It would therefore be desirable to provide a flow control system which can compensate for the failure of solenoid valves to operate properly in controlling gas flow to a tonometer for calibration of a blood gas or pH sensor. Although it would be possible to add backup solenoid valves for each main solenoid valve, it would be desirable to provide a common selector valve which can receive the output flow from two or more supply solenoid valves and select and direct one such output flow to the tonometer. It would also be desirable for the action of the supply solenoid valves and the common selector valve to be coordinated and controlled by a flow control device, to allow the tonometric calibration process to be automated. It would further be desirable that intermediate gas flow valves also select between gas flow of the supplied gas in an open position, and venting of the flow path to the common selector valve to a relatively lower pressure in a closed position to prevent introduction of any mixed calibration gases into the tonometer. It is also desirable to provide the gas flow control system with the capability of supplying three or more different gas compositions to the tonometer for calibration of a multiple sensor. The present invention meets these needs.

SUMMARY OF THE INVENTION

Briefly, and in general terms, the present invention provides for an apparatus for controlling the flow of multiple gases to a tonometer for calibration of a blood gas or pH sensor in which a common selector valve is provided downstream of intermediate gas flow valves, and the intermediate gas supply solenoid valves preferably select between gas flow of the supplied gas in an open position, and venting to a relatively lower pressure in a closed position, to prevent introduction of mixed calibration gases into the tonometer in the event of failure of any one of the valves to close properly.

The invention accordingly provides for an improved gas flow control apparatus for use with a tonometer for calibration of blood gas and pH sensors. The gas flow control apparatus typically includes two or more sources of pressurized gas compositions, gas flow communication means with gas flow valves connected between the sources of gas and the tonometer for controlling gas flow through the flow communication means, and control means for controlling the operation of the valves. A common selector valve, is also preferably connected between the intermediate gas flow valves and the tonometer for selecting for gas flow from one of the intermediate gas flow valves and deselecting gas flow from the other valves to the tonometer. Control means are also provided for controlling the operation of the intermediate valves and the common selector valve.

In one preferred embodiment, two gas sources are provided, with two intermediate gas flow valves which are also selector type valves which select between gas flow from a gas source to the common selector valve in a first open position, and venting to an output having a reduced pressure relative to the pressure of the gas source in a second closed position. In a second preferred embodiment, the gas flow apparatus includes a plurality of gas sources, a plurality of intermediate gas flow valves connected to the gas sources, and a multiple position common selector valve for permitting gas communication between one of the plurality of the intermediate gas flow valves and the tonometer. In an alternative preferred embodiment for a plurality of gas sources, a tree structure of tributary selector valves is connected between the gas sources and the common selector valve.

These and other aspects and advantages of the invention will become apparent from the following detailed description, and the accompanying drawing, which illustrates by way of example the features of the invention.

DETAILED DESCRIPTION OF THE PREFERRED EMBODIMENTS

Incorrect seating of plunger type solenoid valves of gas supply systems for biomedical sensor calibration tonometers can allow gas leakage and incorrect flow rates, due to degradation of the closing spring force of the valves or particles caught between the valve seat and the plunger of the valves. Failure of such valves to properly close can allow a selected calibrating gas composition to mix with one or more unselected calibrating gas compositions, causing significant errors in calibration of sensors in the tonometer. The present invention provides for a gas flow control apparatus for a tonometer which compensates for any such valve failures to prevent calibration errors due to such mixing of calibrating gas compositions.

Figure 1:
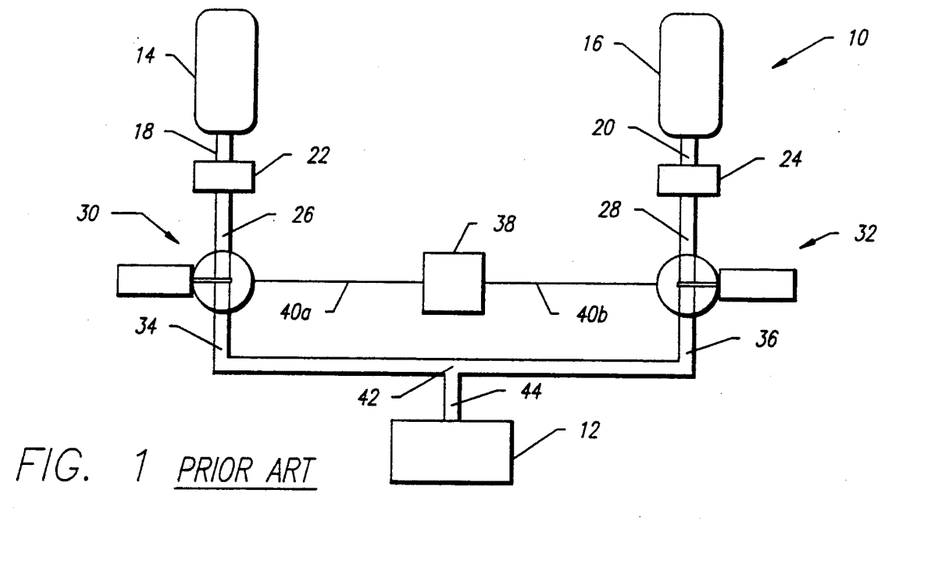
FIG. 1 is a schematic diagram of a prior art gas flow apparatus for a tonometer.

As is shown in FIG. 1, an exemplary prior art gas tonometry system for calibration of biomedical sensors typically includes a gas flow control system 10 for alternate introduction of two different pressurized gas compositions into the tonometer 12 to allow calibration of the sensors at two different gas concentrations or pH's. The prior art system includes a first source 14 of a first pressurized gas composition with a desired partial pressure of a calibration gas, such as carbon dioxide and oxygen, formulated to provide a desired gas concentration and pH in a calibration solution in the tonometer. A second source 16 of a second pressurized gas composition provides a different partial pressure of the calibration gases, in order to allow for a two point calibration of a sensor in the tonometer. The first and second gas sources are connected to first and second respective pressure regulators 22 and 24 through corresponding first and second high pressure gas lines 18 and 20. Gas flow lines 26 and 28 are connected between the regulators and corresponding first and second plunger type solenoid valves 30 and 32, which are in turn connected via the corresponding gas lines 34 and 36 to a manifold 42 to permit gas flow through line 44 to the tonometer. The operation of the first and second solenoid valves is controlled by a control unit 38 via electrical lines 40a and 40b, respectively.

Figure 2:
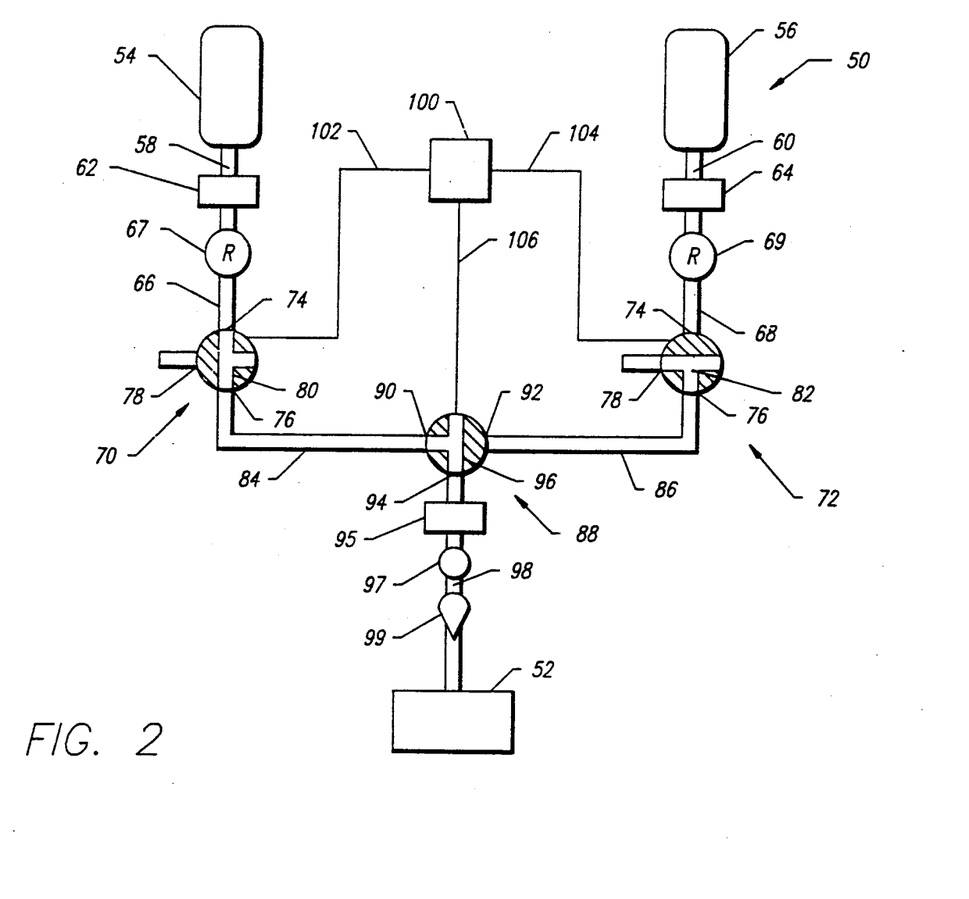
FIG. 2 is a schematic diagram of a first preferred embodiment of the improved gas flow apparatus for a tonometer having two pressurized gas sources.

As is illustrated in FIG. 2, a first preferred embodiment of an improved gas flow control apparatus 50, for use with a tonometer 52 for calibration of a biomedical sensor (not shown), includes at least a first source 54 and a second source 56 of corresponding first and second different pressurized gas compositions with a desired concentration or partial pressure of calibration gases, such as carbon dioxide and oxygen, formulated to provide desired gas concentrations and pH in a calibration fluid in the tonometer. The first and second gas sources are typically high pressure tanks pressurized with gas compositions containing different partial pressures of the calibrating gas, which thus permit a two point calibration of the sensor in the tonometer. To provide a controlled flow of the desired gas compositions to the tonometer, the first and second gas sources are respectively connected via first and second high pressure gas lines 58 and 60 to first and second respective pressure regulators 62 and 64. The pressure regulators provide a moderated pressure flow of the first and second gas compositions at a pressure preferably greater than atmospheric pressure, through first and second respective gas flow lines 66 and 68, which preferably include pressure safety valves 67 and 69, respectively. The first and second gas flow lines 66 and 68 are connected in turn to corresponding first and second intermediate gas selector valves 70 and 72. The intermediate selector valves are preferably electric solenoid actuated, two position selector type valves which are commercially available, and include a single input port 74, a first output port 76 for flow to the tonometer, and a second output port 78 which preferably vents to a relatively lower pressure outlet such as to the atmosphere. In a first open position 80 the input port 74 is connected for gas flow to the first output port 76, so that the valve is open for gas communication to the tonometer. In a second closed position 82 the first output port 76 is connected to the second output port 78, and the valve is closed to prevent gas communication with the tonometer. In this second, closed position, the output port 76 is preferably vented to the atmosphere, which has a pressure relatively lower than the pressure of the supplied gas compositions, so that any leakage of gas through the closed selector valve will be vented to the atmosphere.

Alternatively, the second output port 78 can also be connected to a vacuum source to draw away gases which may leak through the closed selector valve, or other types of reduced pressure vents or containers may also be provided to draw away gas leaking through the closed selector valve, if it is desirable that the gas composition should not be directly vented to the atmosphere.

The first output ports 76 of the gas selector valves 70 and 72 are connected via gas lines 84 and 86, respectively, to a common selector valve 88 to permit gas flow through the tonometer gas flow line 98 to the tonometer 52. The tonometer gas flow line 98 preferably also includes a pressure transducer 95 for measuring gas pressure, a fixed resistor 97, and a needle valve 99 to further accurately control the gas flow to the tonometer 52. The common selector valve is preferably an electrically actuated, solenoid type selector valve which is commercially available, and preferably includes first and second input ports 90 and 92 connected for gas communication via lines 84 and 86 to receive a selected gas from the first and second selector valves, and an output port 94 for communicating the selected gas composition to the tonometer. The common selector valve has a first position 96 in which the output port is connected to the input port 90 to select for gas flow from the first gas selector valve 70 to the tonometer, and a second position (not shown) in which the output port is connect to the input port 92 to select for gas flow from the second gas selector valve 72 to the tonometer. At the same time, the common selector valve preferably prevents gas flow from the unselected gas selector valve.

The operation of the gas selector valves 70 and 72 and the common selector valve is controlled by the control unit 100, which is electrically connected to each of these valves by control lines 102, 104 and 106, respectively. The control unit preferably includes switches under microprocessor control, and may include a timer and a memory for automated equilibration of fluid in the tonometer, although the control unit may alternatively include manually operated switches, or other suitably actuated switches for operation of the gas selector valves and the common selector valve.

It can be readily seen that with the unselected gas selector valve venting the corresponding input port to the reduced pressure at the gas selector vent 78, any gas leakage of the unselected gas composition and/or the selected gas composition through the closed input port of the common selector valve will simply be drawn away from the common selector valve, avoiding the possibility of introduction of a mixture of the two different calibration gases into the tonometer even in the event of leakage through both the closed gas selector valve and the closed port of the common selector valve.

Figure 3:
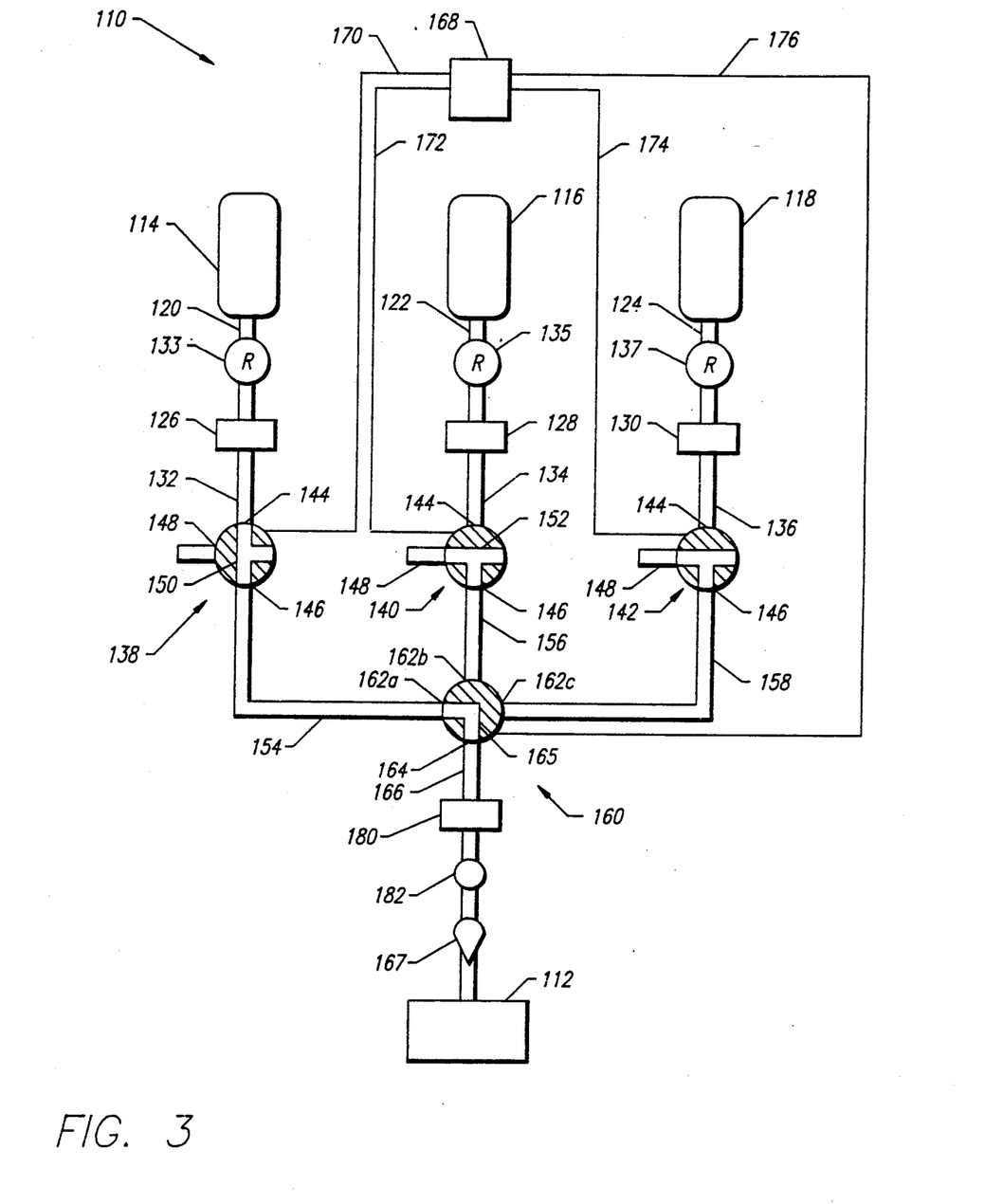
FIG. 3 is a schematic diagram of a second preferred embodiment of the improved gas flow apparatus for a tonometer having multiple pressurized gas sources.

A second preferred embodiment of the improved gas flow control apparatus of the invention utilizing a multiple input port common selector valve permits the use of three or more different gas compositions, as is illustrated in FIG. 3. In this embodiment, the gas flow control apparatus 110 is adapted to introduce any one of the three calibration gas compositions to a tonometer 112 for calibration of a biomedical sensor (not shown). The gas flow control apparatus preferably includes at least a first source 114, second source 116, and a third source 118 of corresponding first, second and third different pressurized gas compositions with a desired concentration or partial pressure of a calibration gas, such as carbon dioxide or oxygen, formulated to provide a desired gas concentration or pH in a calibration fluid in the tonometer. The three pH sources are typically high pressure tanks pressurized with three corresponding different gas compositions, to permit up to a three point calibration of the sensor in the tonometer, or calibration of different types of sensors or multiple sensors in the tonometer. To provide a controlled flow of the desired gas compositions to the tonometer, the three gas sources are respectively connected via three high pressure gas lines 120, 122 and 124 to first, second and third respective pressure regulators 126, 128 and 130. The pressure regulators provide reduced pressure of the three gas compositions at a pressure preferably greater than atmospheric pressure, through three corresponding gas flow liens 132, 134 and 136, which preferably include pressure safety valves 133, 135, 137. The three gas flow lines 132, 134 and 136 are in turn connected to corresponding first, second and third gas composition selector valves 138, 140 and 142. The selector valves are preferably electric solenoid actuated, two position selector type valves which are commercially available, and include a single input port 144, a first output port 146 for flow to the common selector valve for the tonometer, and a second output port 148 which preferably vents to the atmosphere. In a first open position 150 the input port 144 is connected for gas flow to the first output port 146, so that the valve is open for gas communication to the common selector valve. In a second closed position 152 the first output port 146 is connected to the second output port 148, and the valve is closed to gas communication with the common selector valve.

As in the first embodiment, in this second, closed position, the output port 146 is vented to the atmosphere, which is less than the pressure of the supplied gas compositions, so that any leakage of gas through the closed selector valve will be vented to the atmosphere. Alternatively, the second output port 148 can also be connected to a vacuum source to draw away gases which may leak through the closed selector valve, or other types of reduced pressure vents or containers may also be provided to draw away gas leaking through the closed selector valve, if it is desirable that the gas composition should not be directly vented to the atmosphere.

The first output ports 146 of the three gas selector valves 138, 140 and 142 are connected via gas lines 154, 156 and 158, respectively, to a common selector valve 160 to permit selective gas flow to the tonometer. The common selector valve is similar to that of the first embodiment, in that it is preferably an electrically actuated, solenoid type selector valve. However, the common selector valve 160 preferably includes first, second and third input ports 162a,b,c connected for gas communication via lines 154, 156 and 158 to receive a selected gas from the first, second and third gas selector valves, and a single output port 164 for communicating the selected gas composition through the tonometer gas flow line 166 to the tonometer 112. The tonometer gas flow line also preferably includes a pressure transducer 180 for measuring gas pressure in the line to the tonometer, a fixed resistor 182, and a needle valve 167 to further accurately control the flow of gas to the tonometer. The common selector valve has a first position 165 in which the output port 164 is connected to the first input port 162a to select for gas flow from the first gas selector valve 138 to the tonometer, a second position (not shown) in which the output port is connected to the input port 162b to select for gas flow from the second gas selector valve 140 to the tonometer, and a third position (not shown) in which the output port 164 is connected to the third input port 162c. The common selector valve preferably simultaneously deselects or closes off gas flow from the unselected gas selector valves. The operation of the gas selector valves and the common selector valve is preferably controlled by the control unit 168, which is electrically connected to each of these valves by control lines 170, 172, 174, and 176, respectively. The control unit preferably includes switches under microprocessor control, and may include a timer and a memory for automated equilibration of fluid in the tonometer, although the control unit may alternatively include manually operated switches, or other suitably actuated switches for operation of the gas selector valves and the common selector valve.

The principle of operation of the combination of vented gas selector valves and the multi-input port common selector valve is the same as for the first embodiment, in that with the unselected gas selector valve venting the corresponding input port to the reduced pressure at the gas selector vent 78, any gas leakage through the closed input port of the common selector valve will be drawn to a reduced pressure vent, avoiding the possibility of introduction of a mixture of the different calibration gases into the tonometer even in the event of leakage through both the closed gas selector valves and the closed port of the common selector valve.

Figure 4:
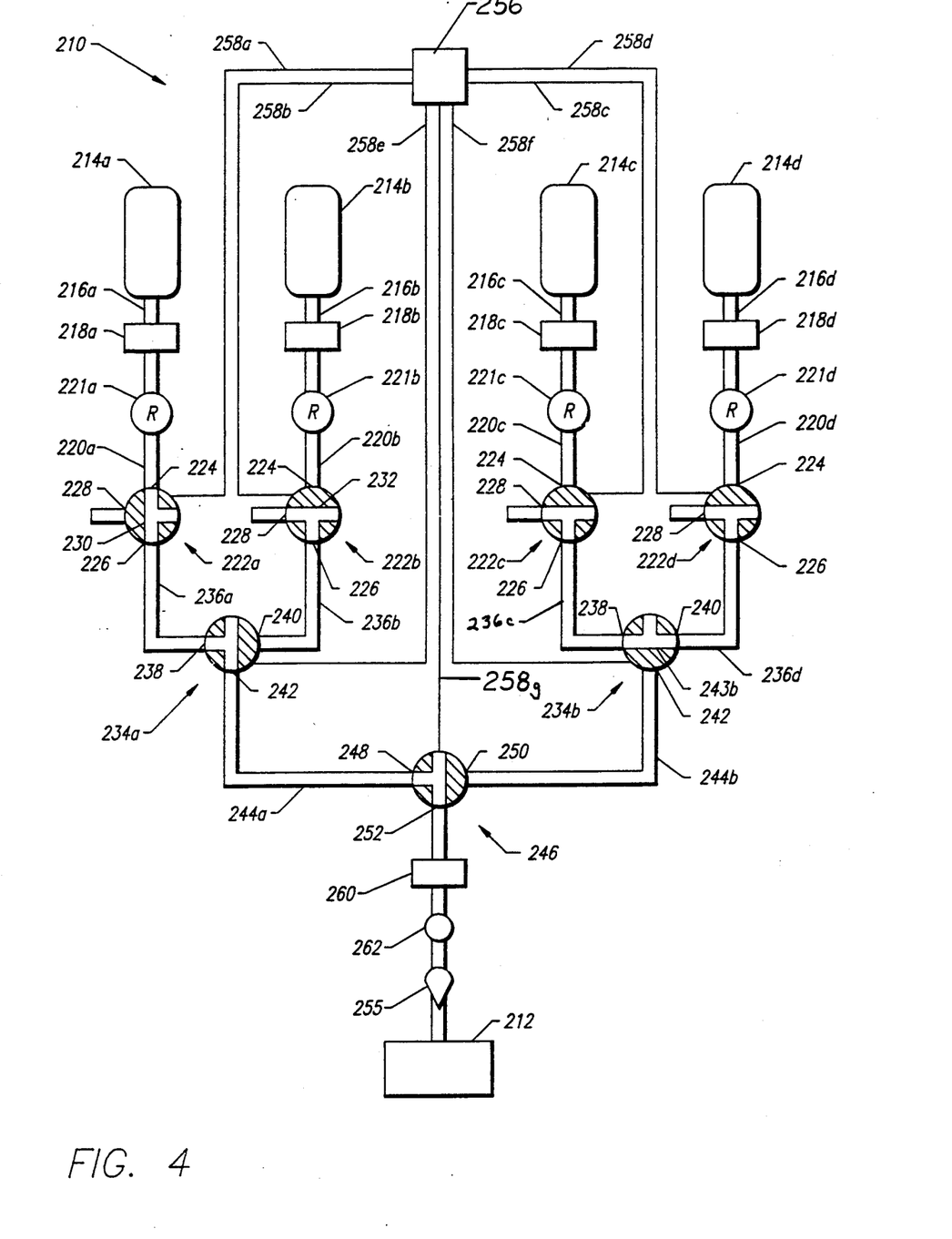
FIG. 4 is a schematic diagram of a third preferred embodiment of the improved gas flow apparatus for a tonometer having multiple pressurized gas sources.

A third preferred embodiment is illustrated in FIG. 4. In this embodiment, the gas flow control apparatus 210 is adapted to introduce any one of the four different calibration gas compositions to a tonometer 212 for calibration of a biomedical sensor (not shown). The gas flow control apparatus includes at least two different calibration gas sources, and as shown, for purposes of illustration, can include four sources 214a,b,c,d of corresponding first, second, third and fourth different pressurized gas compositions with a desired concentration or partial pressure of a calibration gas, such as carbon dioxide or oxygen, formulated to provide a desired gas concentration or pH in a calibration fluid in the tonometer. The four gas sources are typically high pressure tanks pressurized with four corresponding different gas compositions, to permit up to a four point calibration of the sensor in the tonometer, or calibration of multiple sensors or different types of sensors. As will be apparent, additional gas composition sources could also be provided. To provide a controlled flow of the desired gas compositions to the tonometer, the four gas sources are respectively connected via four high pressure gas lines 216a,b,c,d to first, second, third and fourth respective pressure regulators 218a,b,c,d. The pressure regulators provide reduced pressure and control of the four gas compositions at pressures which are preferably greater than atmospheric pressure, through four corresponding gas flow lines 220a,b,c,d, which preferably include safety pressure release valves 221,a,b,c,d, respectively. The four gas flow lines 220a,b,c,d are connected to provide gas flow to a first tier of corresponding first, second, third and fourth primary gas composition selector valves 222a,b,c,d.

As in the previous embodiment, the primary or first tier of gas selector valves 222a, b, c and d are selector valves of the type which are commercially available, and include a single input port 224, a first output port 226 for flow to the common selector valve for the tonometer, and a second output port 228 which preferably vents to the atmosphere. In a first open position 230 the input port 224 is connected for gas flow to the first output port 226, so that the valve is open to provide gas flow. In a second closed position 232 the first output port 226 is connected to the second output port 228, and the valve is closed to prevent gas flow. As in the first and second embodiments, the output port 226 is preferably vented in this second, closed position, to the atmosphere, having a relatively lower pressure than the pressure of the supplied gas compositions, so that any leakage of gas through the closed selector valve will be vented to the atmosphere. Alternatively, the second output port 228 can also be connected to a vacuum source to draw away gases which may leak through the closed selector valve, or other types of reduced pressure vents or containers may also be provided to draw away gas leaking through the closed selector valve, if it is desirable that the gas composition should not be directly vented to the atmosphere.

The first output ports 226 of the four gas selector valves are connected via gas lines 236a,b,c,d, respectively, to a next tier of secondary gas selector valves 234a,b forming a tree structure with other such tertiary or later selector valves, directing the selected gas composition to the tonometer. The secondary gas selector valves are also preferably electric solenoid actuated, two position selector valves of the type which are commercially available, but differ from the first tier of gas selector valves in having first and second input ports 238, 240, to receive gas flow from any one of two primary gas selector valves, and a single output port 242 to be connected to either of the input ports to provide for gas flow communication to the next level of selector valves and to the tonometer. In a first position 243a the first input port 238 is connected for gas flow to the sole output port 242, and in a second position 243b the second input port 240 is connected to the sole output port 242. In this illustration, the third tier of gas selector valves consists of the common selector valve 246 which selects between the gas flow provided from the secondary gas selector valves 234a,b to permit selective gas flow to the tonometer. The common selector valve 246 is essentially identical in structure and operation to the secondary gas selector valves, preferably simultaneously deselecting or closing off gas flow from the unselected gas selector valve of the tier above. Common selector valve 246 preferably includes first and second input ports 248, 250, to receive gas flow from any one of the secondary gas selector valves, and a single output port 252 to be connected to either of the input ports to provide for gas flow communication through tonometer gas flow line 254 to the tonometer 212. The tonometer gas flow line 254 also preferably includes a pressure transducer 260 for measuring gas pressure in the line, a fixed resistor 262, and a needle valve 255 for accurately controlling the flow of gas to the tonometer. The operation of the intermediate gas selector valves and the common selector valve is preferably controlled by the control unit 256, which is electrically connected to each of these valves by control lines 258a-g, respectively. The control unit preferably includes switches under microprocessor control, and may include a timer and a memory for automated equilibration of fluid in the tonometer, although the control unit may alternatively include manually operated switches, or other suitably actuated switches for operation of the primary, secondary and common selector valves.

The principle of operation of the combination of vented primary gas selector valves and the tree structure of secondary selector valves is essentially the same as for the previous two embodiments, in that with the unselected gas selector valves venting the input port of the next tier of selector valves to reduced pressure by way of the vent ports 228 of the primary selector valves, any gas leakage through closed input ports of the next tiers of valves will be drawn to a reduced pressure vent, avoiding the possibility introducing a mixture of the different calibration gases into the tonometer.

It can thus be appreciated that the gas flow apparatus of the invention can compensate for the failure of gas flow valves to operate properly in controlling gas flow to a tonometer apparatus for calibration of blood gas or pH sensors. The placement of the common selector valve in the gas flow path immediately prior to the tonometer to receive the output flow from two or more supply solenoid valves and select and direct one such output flow to the tonometer allows for added control of the selection of calibration gases, even where valves are not closing properly. Venting by the intermediate gas flow valves to reduced pressure or the atmosphere in a closed position further prevents introduction of any mixture of different calibration gas compositions since flow of the deselected gas compositions will be at such weak pressure that flow of the deselected gas compositions to the tonometer will not occur due to greater pressure from the selected gas supply. The control means of the invention further permits the automated calibration of blood gas or pH sensors with multiple calibration points, or calibration of various types of such sensors or multiple sensors.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An improved gas flow control apparatus for use with a tonometer for calibration of biomedical sensors, said gas flow control apparatus including first and second gas supply means for supplying first and second gas compositions under pressure to said tonometer, first and second flow communication means for providing gas flow communication between said first and second gas supply means, respectively, and said tonometer, said first and second flow communication means including first and second respective valve means for controlling gas flow through said flow communication means, and control means for controlling the operation of said first and second valve means, said improved gas flow apparatus comprising:

common selector valve means connected for gas communication between said first and second valve means and said tonometer for selecting gas flow from one of said first and second valve means and deselecting gas flow from the other of said first and second valve means to said tonometer, said common selector valve means including a solenoid valve having a first position for selecting gas communication between said first flow communication means and said tonometer, and a second position for selecting gas communication between said second flow communication means and said tonometer, said control means being connected to said common selector valve means for controlling the operation of said common selector valve means.

2. The improved gas flow apparatus of claim 1, wherein said apparatus includes a plurality of gas supply means for supplying gas compositions under pressure to said tonometer, and a plurality of flow communication means for communicating between respective ones of said plurality of gas supply means and said tonometer, and further including a tree structure of tributary selector valves connecting said plurality of flow communication means to said common selector valve, and wherein said tributary selector valves are operatively connected to said control means.

3. The apparatus of claim 2, wherein said tributary selector valves comprise two position solenoid valves having two selectable inputs and a single output.

4. A gas flow control apparatus for use with a tonometer for calibration of biomedical sensors, said gas flow control apparatus comprising:

a plurality of gas supply means for supplying a plurality of gas compositions under pressure to said tonometer;

a plurality of flow communication means for providing gas flow communication between said plurality of gas supply means, respectively, and said tonometer, said plurality of flow communication means including a plurality of selector valves which select between gas flow of a supplied gas from one of said plurality of gas supply means to said common selector valve means in a first position, and venting to an output having a reduced pressure relative to said pressure of said gas supply means in a second position for controlling gas flow through said flow communication means;

common selector valve means connected for gas communication between a plurality of selector valves; and control means connected to said plurality of selector valves and said common selector valve means for controlling the operation of said selector valves and said common selector valve means.

5. The apparatus of claim 4, wherein said common selector valve means comprises a multiple position solenoid valve having a plurality of positions for selecting for gas communication between one of said plurality of selector valves and said tonometer, and deselecting for gas communication between others of said plurality of selector valves and said tonometer.

6. The apparatus of claim 4, further including a tree structure of tributary selector valves connecting said plurality of selector valves to said common selector valve, and wherein said tributary selector valves are operatively connected to said control means.

7. The apparatus of claim 6, wherein said tributary selector valves comprise two position solenoid valves having two selectable inputs and a single output.

8. The apparatus of claim 11, wherein plurality of selector valves vent to the atmosphere in said second position.

9. An improved gas flow control apparatus for use with a tonometer for calibration of biomedical sensors, said gas flow control apparatus including first and second gas supply means for supplying first and second gas compositions under pressure to said tonometer, first and second flow communication means for providing gas flow communication between said first and second gas supply means, respectively, and said tonometer, and control means for controlling the operation of said first and second flow communication means, said improved gas flow apparatus comprising:

common selector valve means connected for gas communication between said first and second valve means and said tonometer for selecting gas flow from one of said first and second valve means and deselecting gas flow from the other of said first and second valve means to said tonometer, said control means being connected to said common selector valve means for controlling the operation of said common selector valve means; and first and second respective valve means in said first and second flow communication means for controlling gas flow through said flow communication means, said first and second valve means comprising selector valves which select between gas flow of a supplied gas from one of said first and second gas supply means to said common selector valve means in a first position, and venting to an output having a reduced pressure relative to said pressure of said gas supply means in a second position.

10. The improved gas flow apparatus of claim 9, wherein said first and second valve means are two position solenoid valves which select between gas flow of a supplied gas from one of said first and second gas supply means to said common selector valve means in an open position, and venting to an output at a reduced pressure relative to said pressure of said gas supply means in a closed position.

11. The apparatus of claim 10, wherein first and second valve means solenoid valves vent to the atmosphere in said closed position.

12. The improved gas flow apparatus of claim 9, wherein said apparatus includes a plurality of gas supply means for supplying gas compositions under pressure to said tonometer, and a plurality of flow communication means for communicating between respective ones of said plurality of gas supply means and said tonometer, and said common selector valve means comprising a multiple position solenoid valve having a plurality of positions for selecting gas communication between one of said plurality of flow communication means and said tonometer, and deselecting gas communication between others of said plurality of flow communication means and said tonometer.

13. The apparatus of claim 9, wherein first and second valve means selector valves vent to the atmosphere in said second position.

* * * * *

UNITED STATES PATENT AND TRADEMARK OFFICE
CERTIFICATE OF CORRECTION

PATENT NO. : 5,205,322
DATED : April 27, 1993
INVENTOR(S) : Merrick, et al.

It is certified that error appears in the above-indentified patent and that said Letters Patent is hereby corrected as shown below:

On the title page, under item [19], delete "Merick" and insert therefor --Merrick--

On the title page, item [75], delete "Ed Merick" and insert therefor --Edwin B. Merrick-- and delete "Al" and insert --Alan--

Column 2, line 46, delete "Valves" and insert therefor --valves--

Column 5, line 38, delete "pH" and insert therefor --gas--

Column 5, line 51, delete "liens" and insert therefor --lines--

Column 7, line 33, after the word "are" insert therefor --preferably electric solenoid actuated, two position--

Column 10, line 25 (Claim 8, line 1), delete "11" and insert therefor --4--

Signed and Sealed this

Thirteenth Day of September, 1994

Attest:

BRUCE LEHMAN

Attesting Officer

Commissioner of Patents and Trademarks